United States Patent [19]

Papantoniou et al.

[11] 4,030,512
[45] June 21, 1977

[54] HAIR LACQUER OR SETTING LOTION CONTAINING BI- OR TRI-SEQUENCED COPOLYMER

[75] Inventors: Christos Papantoniou, Epinay-sur-Seine; Quintino Gaetani, Bondy, both of France

[73] Assignee: Societe Anonyme dite: L'Oreal, Paris, France

[22] Filed: Dec. 29, 1975

[21] Appl. No.: 645,211

[30] Foreign Application Priority Data

Dec. 30, 1974 Luxembourg .................... 71577

[52] U.S. Cl. .................. 132/7; 8/127.51;
260/29.2 EP; 260/29.2 M; 260/29.2 N;
260/33.4 R; 260/33.4 SB; 424/DIG. 1;
424/DIG. 2; 424/47; 424/71; 424/78; 424/81
[51] Int. Cl.² ................ A45D 7/00; A61K 7/11
[58] Field of Search ............. 424/DIG. 1, DIG. 2,
424/47, 71, 81; 132/7; 260/29.2 EP, 29.2 N,
29.2 M, 33.4 R, 33.4 SB, 824 EP, 824 R, 874,
875, 895, 901; 8/127, 51

[56] References Cited

UNITED STATES PATENTS

| | | | |
|---|---|---|---|
| 3,257,281 | 6/1966 | Maeder | 424/47 |
| 3,907,984 | 9/1975 | Calvert et al. | 424/47 |
| 3,927,199 | 12/1975 | Micchelli et al. | 424/47 |
| 3,934,595 | 1/1976 | Madrange et al. | 132/7 |

Primary Examiner—Sam Rosen
Assistant Examiner—Vera C. Clarke

Attorney, Agent, or Firm—Cushman, Darby & Cushman

[57] ABSTRACT

A hair lacquer or hair setting lotion composition comprises in a cosmetic carrier or vehicle at least one bi- or tri-sequenced copolymer comprising at least one sequence (A) having the formula

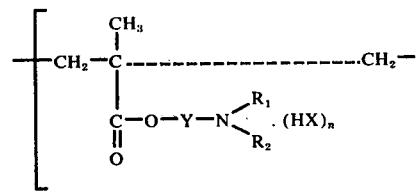

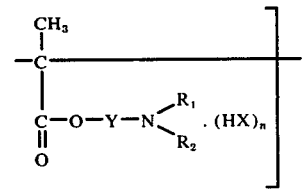

wherein Y is a saturated hydrocarbon chain containing 2–4 carbon atoms or a hydrocarbon chain containing 2–4 carbon atoms and interrupted by sulfur or oxygen, $R_1$ and $R_2$ are alkyl containing 1–4 carbon atoms, $n$ is 0 or 1 and HX is hydrochloric, hydrobromic, lactic or acetic acid, and at least one sequence (B) resulting from the anionic polymerization of a polymerizable monomer.

11 Claims, No Drawings

HAIR LACQUER OR SETTING LOTION CONTAINING BI- OR TRI-SEQUENCED COPOLYMER

The present invention relates to a hair lacquer or hair setting lotion composition containing a sequenced copolymer.

Heretofore numerous synthetic polymers have been proposed for the production of such types of composition. In particular there have been proposed certain heterogeneous as well as homogeneous polymers. It has now been found that sequenced polymers can usefully be employed in the production of hair lacquers and hair setting lotion compositions and, more particularly, bi-sequenced or tri-sequenced copolymers of a particular type. These copolymers are particularly interesting in that by simply varying the nature of the sequences thereof polymers having very different properties can be obtained. This characteristic provides a great advantage particularly in the production of compositions in the form of hair lacquers or hair setting lotions. It is known, for instance, that certain ones of these compositions are prepared in aqueous or hydroalcoholic solutions while others can only be prepared using an alcoholic carrier. The present invention permits the production of these compositions using a wide variety of such carriers.

The sequenced copolymers of the present invention in general carry two or three sequences, each sequence being produced from the same initial monomeric material. The number of sequences, of course, can vary depending upon the ultimate use contemplated.

Thus, the copolymers employed in the present invention are bi- or tri-sequenced copolymers, i.e., the distribution of the monomer units or of the sequences in the polymeric chain can be represented in the following schematic manner:

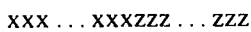   (1)

or in the following manner:

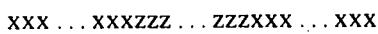   (2)

Accordingly, the present invention relates to a hair lacquer or hair setting lotion composition comprising in an appropriate cosmetic vehicle or carrier at least one bi- or tri-sequenced copolymer including, on the one hand, at least one sequence (A) having the formula:

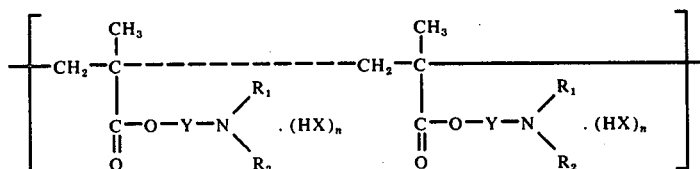

wherein
Y represents a saturated hydrocarbon chain containing 2–4 carbon atoms or a hydrocarbon chain having 2–4 carbon atoms and interrupted by a heteroatom such as sulfur or oxygen;
$R_1$ and $R_2$ each independently represent an alkyl radical having 1–4 carbon atoms,
$n$ is 0 or 1 and HX represents a mineral or organic acid selected from the group consisting of hydrochloric acid, hydrobromic acid, lactic acid and acetic acid, and on the other hand, at least one sequence (B) resulting from the anionic polymerization of a polymerizable monomer.

Preferably, sequence (B), resulting from the anionic polymerization of a polymerizable monomer can be represented by the following formula

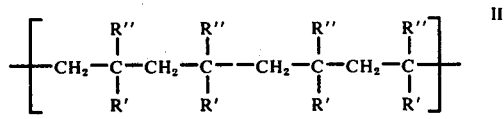

wherein when $R''$ is hydrogen, $R'$ is selected from the group consisting of

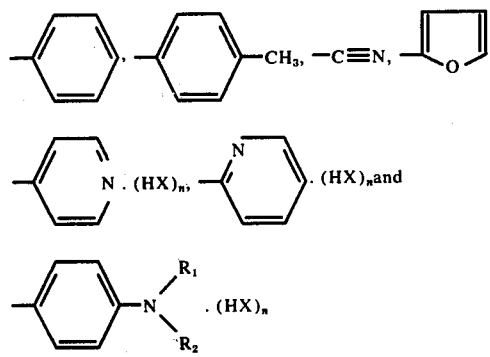

and when $R''$ represents methyl, $R'$ is selected from the group consisting of

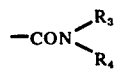

$-COOR_5$ and $-COOH$, wherein $R_1$, $R_2$, $n$ and HX have the same meaning given above, $R_3$ represents a saturated hydrocarbon chain having 6–18 carbon atoms, $R_4$ represents methyl or ethyl and $R_5$ represents a saturated hydrocarbon chain having 1–18 carbon atoms.

In accordance with a preferred embodiment of the present invention, $R'$ represents

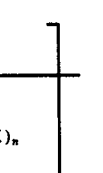

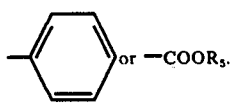

In a variation according to the invention, sequence (B) results from the polymerization of ethylene oxide and can be represented by the formula:

In another variation of the present invention, sequence (B) results from the polymerization of hexamethylcyclo-trisiloxane or from the polymerization of octamethylcyclo-tetrasiloxane and can be represented by the formula

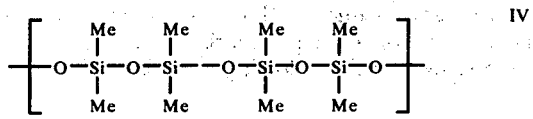

Thus, referring to schematic formulas (1) and (2) above, the bi- and tri-sequenced copolymers of the present invention can take the following forms:

i. AAA — BBB,
ii. AAA — BBB — AAA or
iii. BBB — AAA — BBB wherein the sequence(s) A can correspond to that of formula I and sequence(s) B to that of formulas II, III or IV.

Representative monomers usefully employed in the production of sequences A of formula I include:

2-(N,N-dimethylamino) ethyl methacrylate, 2-(N,N-diethylamino) ethyl methacrylate, 2-[2'(N,N-dimethylamino)ethoxy] ethyl methacrylate and 2-[2'-(N,N-diethylamino) ethoxy] ethyl methacrylate.

Representative monomers usefully employed in the formation of sequence (B) of formula II include:

styrene, 4-methyl styrene, 2-vinyl pyridine, 2-vinyl pyridine hydrochloride, 2-vinyl pyridine lactate, 4-vinyl pyridine, 4-vinyl pyridine hydrochloride, 4-vinyl pyridine lactate, p-dimethylamino styrene, p-dimethylamino styrene hydrochloride, p-dimethylamino styrene lactate, methyl methacrylate, ethyl methacrylate, butyl methacrylate, hexyl methacrylate, octyl methacrylate, lauryl methacrylate, stearyl methacrylate, methacrylonitrile, 2-vinyl furane, and N-methyl-N-lauryl methacrylamide.

When R' in sequence B of formula II represents a carboxylic acid function, this function can be neutralized with a mineral or organic base such as ammonia, monoethanolamine, di-ethanolamine, triethanolamine, isopropanolamine, morpholine, 2-amino-2-methanol propanol-1, 2-amino-2-methyl-1,3-propanediol. Further, this carboxylic acid function can be salified and be present in the form of sodium, potassium or magnesium salt thereof.

In a preferred embodiment of the invention, the tertiary amine functions of sequences A of formula I (i.e. when $n$ is equal to 0), can be quarternized with a quaternization agent selected, for example, from the group of dimethyl sulfate, ethyl bromide and $\beta$-bromo ethanol.

The percentage of the quaternized tertiary amine functions can vary from 0% to 100%, the amount of quaternization being determined as a function of the use of the sequenced polymer.

Similarly, in sequence A of formula I, when $n = 1$, a portion or all of the tertiary amine functions can be salified with the use of a mineral or organic acid and the percentage of salified functions can vary from 0% to 100%.

It has been found that weakly quaternized or salified sequenced polymers are preferably used in aerosol lacquers whereas strongly quaternized or salified sequence polymers are preferably used in an aqueous or hydroalcoholic hair setting lotion composition.

The molecular weight of the bi- and tri-sequenced polymers used in accordance with the present invention can vary widely. The choice of a particular molecular weight value can depend, for instance, on the ultimate use of the copolymer such as in the production of a hair lacquer composition or a hair setting lotion composition.

The bi- and tri-sequenced polymers employed in the present invention have generally a molecular weight ranging between about 1,000 and 1,000,000, but preferably between about 2,000 and 300,000.

As indicated above, the compositions according to the present invention can be present under different forms and principally under the form of a hair setting lotion, a hair lacquer or even under the form of a hair treating composition.

As an example, an aerosol hair lacquer composition can be produced by packaging under pressure in an aerosol container from 0.2 to 5 weight percent of a sequenced polymer of the present invention, from 0 to 35 and preferably from 0 to 25 weight percent of a lower alkanol and from 60 to 99.8 weight percent of a liquified gaseous propellant, such as dichlororodifluoromethane and trichlorofluoromethane and their mixtures.

Preferably, the alkanol is ethyl or isopropyl alcohol.

A hair setting lotion composition in accordance with the present invention can be produced, for example, by admixing a carrier selected from the group consisting of water and a hydroalcoholic solution, containing up to about 60% alcohol, and from 0.2 to 10 weight percent of the sequenced copolymer defined above.

The cosmetic compositions according to the invention can also contain conventional cosmetic adjuvants such as perfumes, dyes, preservatives, plasticizers, thickening agents, anionic, cationic or nonionic products, silicones to improve the brilliance of the hair or other cosmetic resins.

The excellent cosmetic properties of the compositions of the present invention are due to the presence of at least one sequence of formula I in the bi- and tri-sequenced copolymers.

Comparative tests have shown that when the sequence of formula I is replaced by a sequence having a different structure, the sequenced copolymers obtained do not exhibit the advantageous characteristics attained by those used in the present invention when the former are employed in hair lacquer and hair setting lotion compositions because of certain incompatible characteristics they display.

The bi- and tri-sequenced copolymers used in the present invention exhibit, in addition to their excellent solubility and stability in conventional carriers or vehicles for hair lacquer and hair setting lotion compositions, slight or no sensitivity to humidity so that the hair does not become sticky. Further, the composition of the present invention forms a supple film on the hair thus rendering it pleasant to the touch. This film is easily removed by simple brushing or combing.

The present invention also relates to a process for styling the hair, this process comprising applying a sufficient amount of the composition of the present invention to the hair, rolling the hair on hair setting rollers and drying the hair by exposure to external heat for a time ranging from about 3 to 20 minutes.

In accordance with a particular embodiment of this process, the composition is applied immediately after rinsing previously shampooed hair.

Although the process of preparing the sequenced copolymers used in the present invention is known, a principal feature employed in their formation includes polymerizing the initial monomeric reactants in the presence of an anionic polymerization initiator which is in general a metal appearing in the first group of the periodic table of elements such as lithium, sodium, potassium and the like or an organic compound of these metals.

Representative anionic initiators include, for instance, diphenylmethyl sodium, fluorenyl-lithium, fluoroenyl-sodium, naphthalene-sodium, naphthalene-potassium, naphthalene-lithium, tetraphenyl-disodiobutane and phenylisopropyl potassium.

The choice of the polymerization initiator is very important since it influences the structure of the resulting sequenced copolymer. Thus, naphthalene-sodium orients the polymerization towards the production of a tri-sequenced copolymer, while phenylisopropyl potassium or diphenylmethyl sodium orients the polymerization toward the production of a bi-sequenced copolymer.

These polymerization reactions for the formation of sequenced copolymers can take place in an aprotic solvent such as benzene, tetrahydrofuran, toluene and the like.

Generally, the production of the sequenced copolymers is carried out in the following manner. First, a solution of the initiator in the selected solvent is prepared to which there is added one of the monomers required for producing one of the two sequences. After polymerization of this monomer, the second monomer required for the formation of the other sequence is then added.

After the end of the polymerization reaction, the sequenced polymer is rendered inactive by adding to the reaction medium a few drops of a proton-containing solvent such as methanol.

As indicated above, the particular initiator selected orients the reaction towards the formation of a bi- or tri-sequenced polymer.

Generally, the reaction leading to the formation of these sequenced copolymers is effected at a temperature of about −70° C. Further, this reaction obviously can be carried out using monomers having mobile hydrogens, such as acids, amides wherein the nitrogen is unsubstituted, alcohols and compounds containing α-carbonylic hydrogens.

Consequently, when it is desired to obtain sequenced copolymers wherein one of the sequences carries an acid function, it is advisable to start with a monomer which ultimately is capable, through chemical reaction, of forming this type of function. For example, the initial monomer can have an ester function which on hydrolysis yields the corresponding acid.

Such a procedure can be employed when it is desired to produce sequences constituted by a methacrylic acid residue.

The following non-limiting examples are given to illustrate the present invention.

EXAMPLES OF PREPARATION

EXAMPLE 1

Preparation of a lauryl methacrylate-2-N,N-dimethylamino ethyl methacrylate copolymer Into a 4-liter round bottomed flask, fitted with a mechanical agitator, a double dropping funnel, a nitrogen lead-in tube, a descending tube for withdrawing portions of the reaction mixture and a thermometer, there are introduced 2 liters of anhydrous distilled tetrahydrofuran. The flask is then cooled to a temperature of −60° C using a methanol-solid carbon dioxide mixture.

The whole apparatus is under a nitrogen atmosphere which has been carefully purified by heating to 400° C in the presence of a sheet of copper; the nitrogen stream also being purified by passage on anhydrous potassium and on anhydrous magnesium perchlorate.

Through the double funnel there are added, dropwise, with agitation, 12.5 ml of a solution of diphenylmethyl-sodium in tetrahydrofuran (0.8 mole per liter). There are then added, with continued agitation, 100 g of pure lauryl methacrylate over a 15 minute period.

After agitation, there are also added, over a 15 minute period and at the same temperature, i.e. −60° C, 100 g of a 2-N,N-dimethylamino ethyl methacrylate.

The temperature of the reaction mixture rises slightly and when the exothermicity of the polymerization reaction becomes indistinct, the bi-sequenced polymer whose two sequences are constituted by lauryl polymethacrylate and 2-N,N-dimethylamino ethyl polymethacrylate is deactivated. In general, this deactivation is carried out by adding to the reaction mixture several drops of methanol. The solution then becomes practically colorless. The tetrahydrofuran is distilled off and the residual polymer is first dissolved in chloroform and then precipitated by petroleum ether. After two dissolutions in chloroform and two precipitations in petroleum ether, the polymer is dried under reduced pressure.

The expected bi-sequenced copolymer is obtained in a yield of 80%.

Elemental analysis shows that the copolymer comprises 45 weight percent 2-dimethylamino ethyl polymethacrylate and 55 weight percent lauryl polymethacrylate.

The calculated average molecular weight, in toluene, is 80,000. This bi-sequenced copolymer is soluble in a Freon 11/12 mixture (60/40); it is also soluble in absolute ethyl alcohol.

Further this bi-sequenced copolymer can be quaternized by dimethyl sulfate and the resulting quaternized copolymer is also soluble in the said Freon mixture and absolute ethyl alcohol as well as in a 50—50 alcohol-water mixture.

EXAMPLES 2–8 (See Table I)

These bi-sequenced copolymers appearing in Table I have been prepared in accordance with the same operating procedures described above in Example 1.

EXAMPLES 9–12 (See Table II) Tri-sequenced copolymers.

These tri-sequenced copolymers appearing in Table II have been prepared in accordance with the same operating procedures described above in Example 1.

Quaternized or Salified Copolymers

EXAMPLE 13

Into a 500 ml round-bottomed flask, there are introduced 200 g of distilled, anhydrous tetrahydrofuran and 40 g of the sequenced copolymer obtained in accordance with Example 2. After complete dissolution of the copolymer, 3.2 g of distilled dimethyl sulfate are introduced and the resulting solution is agitated for 24 hours at ambient temperature. The tetrahydrofuran is then distilled off under reduced pressure.

There is thus obtained a yield of 95% of the sequenced copolymer which comprises 27.9 weight percent hexyl methacrylate, 55.6 weight percent 2-N,N-dimethylamino ethyl methacrylate and 16.5 weight percent 2-N,N-dimethylamino ethyl methacrylate quaternized with dimethyl sulfate.

EXAMPLES 14–21 (See Table III)

These quaternized polymers appearing in Table III been prepared in accordance with the same operating procedures as described above in Example 13.

EXAMPLES 22–23 (See Table III)

These salified polymers have also been prepared according to the same operating procedures described in Example 13 above.

In Table I:

The catalysts used are the following: (a) diphenylmethyl sodium and (b) phenyl isopropyl potassium. The solvents employed to determine the average molecular weight are (c) toluene and (d) cyclohexanone.

The introduction of ethylene oxide is carried out by bubbling the same into the reaction mixture at 60° C for 4 hours. The active polymer is then deactivated by the addition of water thereto.

After the introduction of octamethylcyclotetra-siloxane, the temperature of the reaction mixture is maintained at 60° C for 4 hours. The polymer is then deactivated by the addition of water thereto.

TABLE I
BI-SEQUENCED COPOLYMERS

| Example | Monomer 1 | Monomer 2 | Quantity (g) Mon 1 | Quantity (g) Mon 2 | Solution of Catalyst in THF (ml) | Quantity of Catalyst (mg) | Yield % | Average Molecular Mass | Elemental Analysis C | Elemental Analysis H | Elemental Analysis N | Weight Ratio of Monomer 1: monomer 2 in the copolymer |
|---|---|---|---|---|---|---|---|---|---|---|---|---|
| 2 | Hexylmethacrylate | N,N-dimethylaminoethyl methacrylate | 135 | 130 | 60 | 2,865 (a) | 75 | 36,000(c) | 64.0 | 9.9 | 6.3 | 30/70 |
| 3 | Butylmethacrylate | N,N-dimethylaminoethyl methacrylate | 132 | 130 | 60 | 2,865 (a) | 85 | 24,000(c) | 63.1 | 9.9 | 5.9 | 34/66 |
| 4 | Methylmethacrylate | N,N-dimethylaminoethyl methacrylate | 130 | 130 | 60 | 2,865 (a) | 80 | 24,000(c) | 60.8 | 9.0 | 4.1 | 54/46 |
| 5 | Styrene | N,N-dimethylaminoethyl methacrylate | 100 | 50 | 60 | 474 (b) | 76 | 125,400(c) | 82.6 | 8.4 | 2.7 | 69/31 |
| 6 | Butylmethacrylate | N,N-dimethyl-aminoethyl methacrylate | 250 | 150 | 40 | 3,820 (a) | 78 | 31,600(d) | 64.5 | 9.1 | 3.6 | 60/40 |
| 7 | N,N-dimethylamino ethyl methacrylate | Ethylene oxide | 50 | 50 | 10 | 955 (a) | 55 | | | | | 89/11 |
| 8 | N,N-dimethylamino ethyl methacrylate | Octamethylcyclotetra siloxane | 50 | 50 | 10 | 955 (a) | 63 | | | | | 77/23 |

TABLE II
TRI-SEQUENCED COPOLYMERS

| Example | Monomer 1 | Monomer 2 | Quantity (g) Mon 1 | Quantity (g) Mon 2 | Solution of Catalyst in THF (ml) | Quantity of Catalyst (mg) | Yield % | Average Molecular Mass | Elemental Analysis C | Elemental Analysis H | Elemental Analysis N | Weight Ratio of Monomer 1 Monomer 2 in the copolymer |
|---|---|---|---|---|---|---|---|---|---|---|---|---|
| 9 | Butylmethacrylate | N,N-dimethylamino ethyl methacrylate | 70 | 70 | 35 | 2,640 (e) | 80 | 31,800(d) | 65.9 | 8.8 | 4.8 | 46/54 |
| 10 | Butylmethacrylate | N,N-dimethylamino ethyl methacrylate | 250 | 150 | 200 | 8,120 (f) | 75 | 22,000(d) | 64.9 | 9.4 | 3.5 | 60/40 |
| 11 | Styrene | N,N-dimethylamino ethyl methacrylate | 35 | 35 | 20 | 1,510 (e) | 85 | 45,600(d) | 76.9 | 8.9 | 4.1 | 54/46 |
| 12 | N,N-dime- | Butyl | 60 | 140 | 200 | 4,060 (f) | 65 | 70,000 (c) | 64.2 | 9.2 | 3.8 | 43/57 |

TABLE II-continued
TRI-SEQUENCED COPOLYMERS

| Example | Monomer 1 | Monomer 2 | Quantity (g) Mon 1 | Mon 2 | Solution of Catalyst in THF (ml) | Quantity of Catalyst (mg) | Yield % | Average Molecular Mass | Elemental Analysis C H N | Weight Ratio of Monomer 1 Monomer 2 in the copolymer |
|---|---|---|---|---|---|---|---|---|---|---|
| | thylamino ethyl methacrylate | methacrylate | | | | | | | | |

Initiator:
(e) : Naphtalene sodium
(f) : 1,1-diphenyl ethylene sodium
Polymers 9 – 11 are of the type: AAA-BBB-AAA
Polymer 12 is of the type: BBB-AAA-BBB
Solvent in which the measurement has been made:
(c) toluene
(d) cyclohexanone

TABLE III
QUATERNIZED POLYMERS

| Example | Polymer of Example Used No | Weight (g) | Quaternization Agent (g) | % of Quaternization or of salification | Yield % | Composition of polymer obtained g/100g | |
|---|---|---|---|---|---|---|---|
| 14 | 3 | 40 | 3.2(a) | 15.1 | 95 | Butylmethacrylate | 31.5 |
| | | | | | | 2-N,N-dimethylamino ethyl methacrylate | 51.9 |
| | | | | | | Quaternized 2-N,N-dimethylamino ethyl methacrylate | 16.6 |
| 15 | 4 | 40 | 3.2(a) | 21.7 | 95 | Methylmethacrylate | 50.1 |
| | | | | | | 2-N,N-dimethylamino ethyl methacrylate | 33.4 |
| | | | | | | Quaternized 2-N,N-dimethylamino ethyl methacrylate | 16.6 |
| 16 | 1 | 40 | 3.2(a) | 19.2 | 90 | Lauryl methacrylate | 51.0 |
| | | | | | | 2-N,N-dimethylamino-2 ethyl methacrylate | 32.4 |
| | | | | | | Quaternized 2-N,N-dimethylamino ethyl methacrylate | 16.6 |
| 17 | 6 | 40 | 3.2(a) | 25 | 95 | Butylmethacrylate | 55.6 |
| | | | | | | 2-N,N-dimethylamino ethyl methacrylate | 27.8 |
| | | | | | | Quaternized 2-N,N-dimethylamino ethyl methacrylate | 16.6 |
| 18 | 9 | 10 | 0.8(a) | 18.5 | 95 | Butylmethacrylate | 42.6 |
| | | | | | | 2-N,N-dimethylamino ethyl methacrylate | 40.8 |
| | | | | | | Quaternized 2-N,N-dimethylamino ethyl methacrylate | 16.6 |
| 19 | 9 | 10 | 0.79(b) | 18.5 | 90 | Butylmethacrylate | 42.6 |
| | | | | | | 2-N,N-dimethylamino ethyl methacrylate | 40.8 |
| | | | | | | Quaternized 2-N,N-dimethylamino ethyl methacrylate | 16.6 |
| 20 | 9 | 10 | 0.69(c) | 18.5 | 90 | Butylmethacrylate | 43 |
| | | | | | | 2-N,N-dimethylamino ethyl methacrylate | 41.2 |
| | | | | | | Quaternized 2-N,N-dimethylamino ethyl methacrylate | 15.8 |
| 21 | 10 | 40 | 0.8(a) | 25 | 95 | Butylmethacrylate | 55.6 |
| | | | | | | 2-N,N-dimethylamino ethyl methacrylate | 27.8 |
| | | | | | | Quaternized 2-N,N-dimethylamino ethyl methacrylate | 16.6 |
| 22 | 9 | 10 | 0.46(d) | 37 | 96 | Butylmethacrylate | 44 |
| | | | | | | 2-N,N-dimethylamino ethyl methacrylate | 32.5 |
| | | | | | | Salified 2-N,N-dimethylamino ethyl methacrylate | 23.5 |
| 23 | 9 | 10 | 1.14(e) | 37 | 95 | Butylmethacrylate | 41.3 |
| | | | | | | 2-N,N-dimethylamino ethyl methacrylate | 30.5 |
| | | | | | | Salified 2-N,N-dimethylamino ethyl methacrylate | 28.2 |

Quaternization or Salification Agent
(a) : dimethyl sulfate
(b) : β-bromoethanol
(c) : ethyl bromide
(d) : hydrochloric acid
(e) : lactic acid

EXAMPLES OF COMPOSITION

EXAMPLE A

A hair setting lotion composition in accordance with the invention is prepared by mixing the following components:

| | |
|---|---|
| Sequenced copolymer of Example 1 | 2 g |
| Ethyl alcohol | 50 g |
| Water, q.s.p. | 100 g |

After application of this hair setting lotion to the hair, the hair is rolled up on hair setting rollers and dried under a hood. An excellent setting of the hair is thus obtained and the hair is supple and pleasant to the touch.

Example A was repeated except that the sequenced copolymer of Example 1 was replaced by an equivalent amount of the sequenced copolymer of Examples 2, 3, 7, 8, 13, 14, 16, 17, 19, 20, 21, 22 and 23.

EXAMPLE B

In accordance with the present invention, a hair lacquer composition is prepared by admixing the following components:

Sequenced copolymer of

-continued

| | |
|---|---|
| Example 1 | 8 g |
| Ethyl alcohol, q.s.p. | 100 g |

25 g of this solution are packaged in an aerosol container under pressure together with 45 g of trichlorofluoromethane and 30 g of dichlorodifluoromethane.

Example B was repeated except that the sequenced copolymer of Example 1 was replaced by an equivalent amount of the sequenced copolymer of Examples 2, 3, 4, 5, 11, 12, 13, 14, 15, 16, 17, 18 and 21.

EXAMPLE C

In accordance with the present invention, a hair lacquer composition was prepared by mixing together the following components:

| | |
|---|---|
| Bi-sequenced copolymer of Example 1 | 2 g |
| Trichlorofluoromethane | 45 g |
| Dichlorodifluoromethane | 40 g |

This composition is packaged under pressure in a conventional aerosol container.

EXAMPLE D

A hair setting lotion composition was prepared by admixing the following components:

| | |
|---|---|
| Bi-sequenced copolymer of Example 2 | 2 g |
| Ethyl alcohol | 50 g |
| Water, q.s.p. | 100 g |

After having shampooed and rinsed the hair, the above hair setting lotion is applied uniformly thereto. The hair is then rolled up on hair setting rollers and dried. This treatment produced beautiful curls exhibiting excellent holding power over an extended period.

Example D was repeated except that the sequenced copolymer of Example 2 was replaced by an equivalent amount of the sequenced copolymer of Examples 3, 4, 13 and 14.

EXAMPLE E

In accordance with the present invention, a hair lacquer composition is produced by admixing the following components:

| | |
|---|---|
| Bi-sequenced copolymer of Example 2 | 8 g |
| Isopropyl alcohol, q.s.p. | 100 g |

25 g of this solution are packaged under pressure in an aerosol container together with 45 g of trichlorofluoromethane and 30 g of dichlorodifluoromethane.

Example E was repeated except that the sequenced copolymer of Example 2 was replaced by an equivalent amount of the sequenced copolymer of Examples 3, 4, 13 and 14.

EXAMPLE F

A hair setting lotion composition is prepared by admixing the following components:

| | |
|---|---|
| Bi-sequenced copolymer of Example 14 | 2 g |
| Isopropyl alcohol | 50 g |
| Water, q.s.p. | 100 g |

EXAMPLE G

A hair setting lotion composition in accordance with the present invention is prepared by admixing the following components:

| | |
|---|---|
| Bi-sequenced copolymer of Example 16 | 2 g |
| Ethyl alcohol | 50 g |
| Perfume | 0.1 g |
| Water, q.s.p. | 100 g |

Immediately after rinsing previously shampooed hair, the above hair lotion composition is applied thoroughly to the hair. The hair is then rolled up on hair setting rollers and dried for 15 minutes. The hair setting obtained has excellent holding power and the hair is shiny and soft to the touch.

EXAMPLE H

A hair lacquer composition is prepared by admixing the following components:

| | |
|---|---|
| Bi-sequenced copolymer of Example 2 | 2 g |
| Trichlorofluoromethane | 45 g |
| Dichlorodifluoromethane | 40 g |

The above composition is packaged under pressure in an aerosol container.

Example H was repeated except that the sequenced copolymer of Example 2 was replaced by an equivalent amount of the sequenced polymer of Examples 3, 4, 13 and 14.

EXAMPLE I

A hair lacquer composition is prepared by admixing the following components:

| | |
|---|---|
| Bi-sequenced copolymer of Example 15 | 8 g |
| Ethyl alcohol, q.s.p. | 100 g |

25 g of the above solution are introduced into an aerosol container together with 45 g of trichlorofluoromethane and 30 g of dichlorodifluoromethane.

EXAMPLE J

A hair lacquer composition is prepared by packaging under pressure in an aerosol container an admixture of the following components:

| | |
|---|---|
| Polymer of Example 1 | 2 g |
| Trichlorofluoromethane | 59 g |
| Dichlorodifluoromethane | 39 g |

Example J was repeated except that the copolymer of Example 1 was replaced by an equivalent amount of the polymer of Examples 2, 3, 5, 11, 13, 16, 17 and 21.

EXAMPLE K

A hair lacquer composition is prepared by packaging the following components under pressure in an aerosol container:

| | |
|---|---|
| Copolymer of Example 5 | 2 g |
| Isopropyl alcohol | 23 g |
| Trichlorofluoromethane | 45 g |
| Dichlorodifluoromethane | 30 g |

Example K was repeated except that the copolymer of Example 5 was replaced by an equivalent amount of the copolymer of Example 11.

EXAMPLE L

A hair lacquer composition was prepared by packaging an admixture of the following components under pressure in an aerosol container:

| | |
|---|---|
| Copolymer of Example 17 | 1.25 g |
| Ethyl alcohol | 48.75 g |
| Nitrous oxide (5 bars) | 2 g |

EXAMPLE M

A hair lacquer composition is prepared by packaging an admixture of the following components under pressure in an aerosol container:

| | |
|---|---|
| Copolymer of Example 21 | 1 g |
| Ethyl alcohol | 49 g |
| $CO_2$ (5 bars) | 2 g |

EXAMPLE N

A hair lacquer composition is prepared by packaging under pressure an admixture of the following components:

| | |
|---|---|
| Copolymer of Example 21 | 1 g |
| Isopropyl alcohol | 49 g |
| $CO_2$ (5 bars) | 1.6 g |

What is claimed is:

1. A hair lacquer or hair setting lotion composition comprising in a solvent selected from the group consisting of water, ethanol, isopropanol, a liquified gaseous propellant, and a mixture thereof, 0.2 to 10 percent by weight of a bi- or tri-sequenced copolymer, the sequences in the chain of said copolymer having a schematic formula selected from the group consisting of i. AAA—BBB
ii. AAA—BBB—AAA and
iii. BBB—AAA—BBB, A having the formula $$\left[ -CH_2-\underset{\underset{O}{\overset{\|}{C}-O-Y-N\langle\underset{R_2}{\overset{R_1}{}}\cdot(HX)_n}}{\overset{CH_3}{|}} -CH_2-\underset{\underset{O}{\overset{\|}{C}-O-Y-N\langle\underset{R_2}{\overset{R_1}{}}\cdot(HX)_n}}{\overset{CH_3}{|}} \right]$$

wherein
Y represents a saturated hydrocarbon chain having 2–4 carbon atoms or a hydrocarbon chain having 2–4 carbon atoms and interrupted by a heteroatom selected from the group consisting of sulfur and oxygen,
$R_1$ and $R_2$ each independently represent alkyl having 1–4 carbon atoms,
$n$ is 0 or 1 and
HX represents an acid selected from the group consisting of hydrochloric acid, hydrobromic acid, lactic acid and acetic acid,
B having a formula selected from the group consisting of (a) $\left[ -CH_2-\underset{R'}{\overset{R''}{|}}C-CH_2-\underset{R'}{\overset{R''}{|}}C\cdots CH_2-\underset{R'}{\overset{R''}{|}}C-CH_2-\underset{R'}{\overset{R''}{|}}C- \right]$ wherein when R″ is hydrogen, R′ is selected from the group consisting of —C₆H₄—, —C₆H₄—CH₃, —C≡N, furyl, pyridyl·(HX)ₙ, pyridyl,
·(HX)ₙ and —C₆H₄—N⟨$\overset{R_1}{R_2}$·(HX)ₙ, and
when R″ is $CH_3$, R′ is selected from the group consisting of —CON⟨$\overset{R_3}{R_4}$, —COOR₅ and —COOH, wherein $R_1$, $R_2$, $n$ and HX have the meanings given above, $R_3$ is a saturated hydrocarbon chain having 6–18 carbon atoms, $R_4$ is methyl or ethyl and $R_5$ is a saturated hydrocarbon chain having 1–18 carbon atoms, b. $-\!\!\left[ O-CH_2-CH_2-O-CH_2-CH_2\ -\ -\ -\ O-CH_2-CH_2-O-CH_2-CH_2 \right]\!\!-$ and (c) 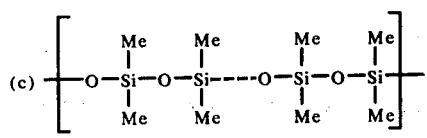

said bi- or tri-sequenced copolymer having a molecular weight between 1,000 and 1,000,000.

2. The composition of claim 1 wherein sequence (A) is the polymerizate of a monomer selected from the group consisting of 2-(N,N-dimethylamino) ethyl methacrylate, 2-(N,N-diethylamino) ethyl methacrylate, 2-[2'-(N,N-dimethylamino) ethoxy]ethyl methacrylate and 2-[2'-(N,N-diethylamino) ethoxy] ethyl methacrylate.

3. The composition of claim 1 wherein when $n = 0$ in sequence (A) the tertiary amine functions are quaternized in an amount of 0–100% with a quaternization agent.

4. The composition of claim 3 wherein said quaternization agent is selected from the group consisting of dimethyl sulfate, ethyl bromide and β-bromo ethanol.

5. The composition of claim 1 wherein sequence (B) is the polymerizate of a monomer selected from the group consisting of styrene, 4-methyl styrene, 2-vinyl pyridine, 2-vinyl pyridine hydrochloride, 2-vinyl pyridine lactate, 4-vinyl pyridine, 4-vinyl pyridine hydrochloride, 4-vinyl pyridine lactate, p-dimethyl aminostyrene, p-dimethyl amino styrene hydrochloride, p-dimethyl amino styrene lactate, methyl methacrylate, ethyl methacrylate, butyl methacrylate, hexyl methacrylate, octyl methacrylate, lauryl methacrylate, stearyl methacrylate, methacrylonitrile, 2-vinyl furan and N-methyl-N-lauryl methacrylate.

6. The composition of claim 1 wherein when R' in sequence B is a carboxylic acid function, said function is neutralized with a base selected from the group consisting of ammonia, monoethanolamine, diethanolamine, triethanolamine, isopropanolamine, morpholine, 2-amino-2-methyl propanol-1,2-amino-2-methyl propanediol-1,3.

7. The composition of claim 1 wherein when R' in sequence B is a carboxylic acid function, said function is in the form of a salt of sodium, potassium or magnesium.

8. The composition of claim 1 wherein said bi- or tri-sequenced copolymer has a molecular weight between 2,000 and 300,000.

9. The composition of claim 1 packaged under pressure in an aerosol container and containing between 0.2 – 5 weight percent of said bi- or tri-sequenced copolymers, from 0–35 weight percent ethanol or isopropanol and from 60 – 99.8 weight percent of a liquified gaseous aerosol propellant.

10. The composition of claim 9 wherein said ethanol or isopropanol is present in an amount of 0–25 weight percent.

11. A process for styling or setting the hair comprising applying to the hair an effective amount of the composition of claim 1, rolling the hair on rollers and applying external heat to the hair for a period of time ranging from 3 to 20 minutes to dry the same.

* * * * *